US008889836B2

(12) United States Patent
Supattapone et al.

(10) Patent No.: US 8,889,836 B2
(45) Date of Patent: Nov. 18, 2014

(54) METHOD FOR NON-COVALENT IMMOBILIZATION OF INFECTIOUS PRION PROTEIN

(75) Inventors: Surachai Supattapone, Hanover, NH (US); Michael B. Miller, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 81 days.

(21) Appl. No.: 13/702,673

(22) PCT Filed: Jun. 8, 2011

(86) PCT No.: PCT/US2011/039573
§ 371 (c)(1), (2), (4) Date: Dec. 7, 2012

(87) PCT Pub. No.: WO2011/159529
PCT Pub. Date: Dec. 22, 2011

(65) Prior Publication Data

US 2013/0085263 A1 Apr. 4, 2013

Related U.S. Application Data

(60) Provisional application No. 61/354,821, filed on Jun. 15, 2010.

(51) Int. Cl.

| | |
|---|---|
| ***A61K 38/17*** | (2006.01) |
| ***C07K 17/14*** | (2006.01) |
| ***G01N 33/53*** | (2006.01) |
| ***G01N 33/551*** | (2006.01) |
| ***G01N 27/00*** | (2006.01) |
| ***C07K 17/00*** | (2006.01) |
| ***G01N 33/543*** | (2006.01) |
| ***G01N 33/68*** | (2006.01) |
| *B82Y 5/00* | (2011.01) |

(52) U.S. Cl.
CPC . *C07K 17/00* (2013.01); *B82Y 5/00* (2013.01); *G01N 33/54326* (2013.01); *G01N 33/6896* (2013.01); *G01N 2800/2828* (2013.01); *Y10S 977/705* (2013.01); *Y10S 977/838* (2013.01); *Y10S 977/904* (2013.01); *Y10S 977/92* (2013.01)
USPC ........... 530/412; 530/304; 530/323; 977/705; 977/838; 977/904; 977/920

(58) Field of Classification Search
None
See application file for complete search history.

(56) References Cited

U.S. PATENT DOCUMENTS

| | | | | |
|---|---|---|---|---|
| 6,916,419 | B2 | 7/2005 | Prusiner et al. | 210/263 |
| 2003/0219801 | A1 | 11/2003 | Lipshutz | 435/6.11 |
| 2004/0052833 | A1 | 3/2004 | Prusiner et al. | 424/442 |

OTHER PUBLICATIONS

Jackson et al., PNAS, 98(15):8531-8535, Jul. 17, 2001.*
Polymenidou et al., PLOS one 3(2):e3872, Dec. 2008.*
Hermentin et al., Bioconjugate Chem., 1(6):411-418, 1990.*
Miller et al, Journal of Virology, 85(6):2813, Jan. 12, 2011.*
International Report on Patentability from PCT/US11/39573, filed Jan. 3, 2013.
Kouassi, G. K. and Irudayarajm J. "A Nanoparticle-based Immobilization Assay for Prion-Kinetics Study" Journal of Nanobiotechnology 2006 4:8.
International Search Report from PCT/US11/39573, filed Nov. 4, 2011.

* cited by examiner

*Primary Examiner* — Daniel E Kolker
*Assistant Examiner* — Stacy N MacFarlane
(74) *Attorney, Agent, or Firm* — Licata & Tyrrell P.C.

(57) ABSTRACT

The present invention is method for non-covalently immobilizing an infectious prion protein using a magnetic substrate.

6 Claims, 6 Drawing Sheets

METHOD FOR NON-COVALENT IMMOBILIZATION OF INFECTIOUS PRION PROTEIN

INTRODUCTION

This application is a U.S. National Stage Application of PCT/US2011/039573 filed Jun. 8, 2011 and claims the benefit of priority of U.S. Provisional Application No. 61/354,821, filed Jun. 15, 2010, the contents of each of which is incorporated herein by reference in their entirety.

This invention was made with government support under grant number R01 NS046478 awarded by National Institutes of Health. The government has certain rights in the invention.

BACKGROUND OF THE INVENTION

Prion diseases are fatal neurodegenerative illnesses that occur in genetic, sporadic and infectious forms (Glatzel, et al. (2005) *Arch. Neurol.* 62:545-552). From a public health perspective, prion diseases are challenging to control because infectious prions are highly resistant to environmental degradation (Brown & Gajdusek (1991) *Lancet* 337:269-270) and can potentially be transmitted by several different routes (Holada, et al. (2000) *Lancet* 356:1772; Ligios, et al. (2005) *Nat. Med.* 11:1137-1138; Mathiason, et al. (2006) *Science* 314:133-136; Seeger, et al. (2005) *Science* 310:324-326). The critical molecular event in the pathogenesis of prion diseases is the misfolding of the host-encoded prion protein ($PrP^{C}$) into an infectious isoform ($PrP^{Sc}$), but the mechanism of this conformational change remains unknown (Prusiner (1982) *Science* 216:136-144). Mature PrP molecules contain 208 amino acid residues, two N-linked glycosylation sites, an intramolecular disulfide bond and a C-terminal glycophosphatidylinositol anchor (Endo, et al. (1989) *Biochemistry* 28:8380-8388; Locht, et al. (1986) *Proc. Natl. Acad. Sci. USA* 83:6372-6376; Stahl, et al. (1987) *Cell* 51:229-240; Turk, et al. (1988) *Eur. J. Biochem.* 176:21-30). Purified native $PrP^{C}$ molecules containing only prion protein and co-purified lipids have been converted into infectious $PrP^{Sc}$ molecules de novo, through an in vitro reaction requiring accessory polyanions (Deleault, et al. (2007) *Proc. Natl. Acad. Sci. USA* 104:9741-9746).

Mammalian prions occur in a variety of different "strains". Strains are defined as natural isolates of infectious prions characterized by distinctive clinical and neuropathological features, which are faithfully recapitulated upon serial passage within the same animal species (Bruce (1993) *Br. Med. Bull.* 49:822-838; Carlson (1996) *Curr. Top. Microbial. Immunol.* 207:35-47). Strain diversity is associated with variations in $PrP^{Sc}$ conformation (Bessen & Marsh (1992) *J. Viral.* 66:2096-2101; Collinge, et al. (1996) *Nature* 383:685-690; Peretz, et al. (2001) *Protein Sci.* 10:854-863; Safar, et al. (1998) *Nat. Med.* 4:1157-1165; Telling, et al. (1996) *Science* 274:2079-2082), but it remains unknown precisely which $PrP^{Sc}$ conformers or domains are required to encode mammalian prion strain phenotypes.

Various methodologies have been developed to analyze and detect the various forms of PrP. For example, conformation-dependent immunoassays (CDI) have shown that prion-infected brains contain both protease-sensitive and protease-resistant $PrP^{Sc}$ molecules (Safar, et al. (1998) supra). In addition, chemical cross-linking of recombinant PrP to nanoparticles has been suggested for use in in vivo and in vitro manipulation of prion proteins to facilitate structural analysis (Kouassi & Irudayaraj (2006) *J. Nanobiotech.* 4:8).

SUMMARY OF THE INVENTION

The present invention is a method for immobilizing an infectious prion protein by contacting the infectious prion protein, e.g., in a biological sample, with a magnetic substrate. In particular embodiments, immobilization is non-covalent and is carried out in the absence of a cross-linking agent. In some embodiments, the magnetic substrate is silanized and/or composed of an iron oxide. In other embodiments, the magnetic substrate is a microparticle, nanoparticle, or nanopowder.

BRIEF DESCRIPTION OF THE DRAWINGS

FIG. 3 shows binding specificity of MAGNABIND beads. Binding of $PrP^{Sc}$ and $PrP^{C}$ molecules to MAGNABIND Protein A. RML scrapie-infected or uninfected mouse brain homogenates were incubated with MAGNABIND Protein A beads for two hours in tris-buffered saline with 3% NP-40 and 3% TWEEN 20.

DETAILED DESCRIPTION OF THE INVENTION $PrP^{C}$ is known in the art as the naturally expressed glycoprotein $PrP^{C}$, also known as PrP-sen, which is found in the neurons of mammals. Not to be held to any particular mechanism of action, it is believed that contact between $PrP^{C}$ and an infectious prion or $PrP^{Sc}$ brings about a conformational change in $PrP^{C}$, converting it from a protein primarily composed of alpha-helices to a protein primarily composed of beta-sheets. This conversion creates a protease resistant, prion protein (i.e., $PrP^{Sc}$, PrP-res) associated with prion disease. Therefore, the term “infectious prion protein” is intended to mean a prion protein which is protease resistant and causes a prion-associated disease.

Figure 1:
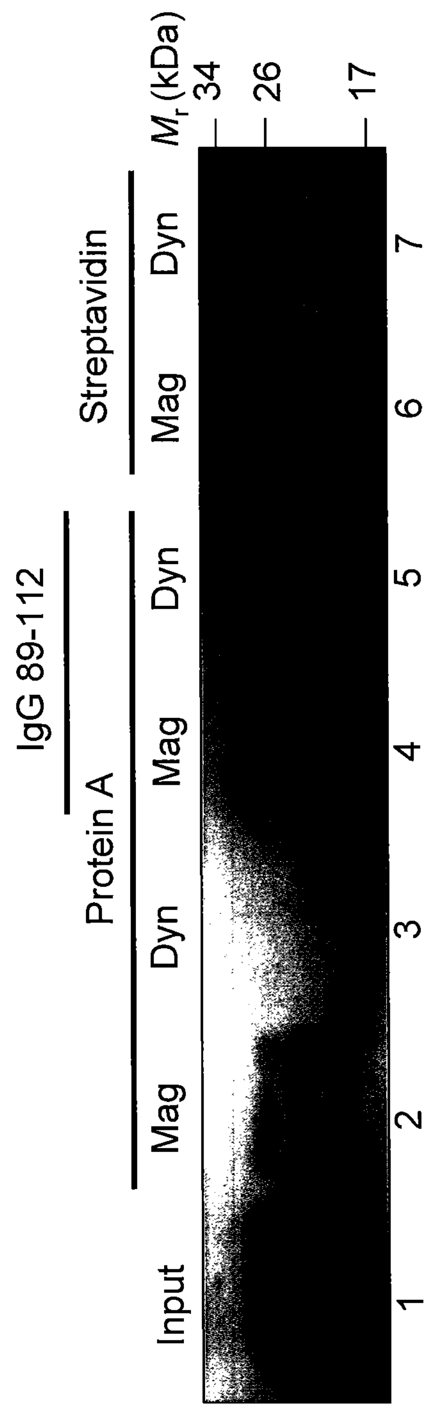
FIG. 1 shows binding of $PrP^{Sc}$ to MAGNABIND beads. RML scrapie-infected mouse brain homogenate was incubated with MAGNABIND (Mag, lanes 2, 4, and 6) or DYNAL (Dyn, lanes 3, 5, and 7) magnetic beads bearing Protein A or Streptavidin. One set of Protein A reactions (lanes 3-4) was co-incubated with IgG 89-112, which recognizes $PrP^{Sc}$. Following incubation, beads were washed, subjected to Proteinase K digestion, and bound molecules were analyzed by anti-PrP (6D11) immunoblot.
Figure 2:
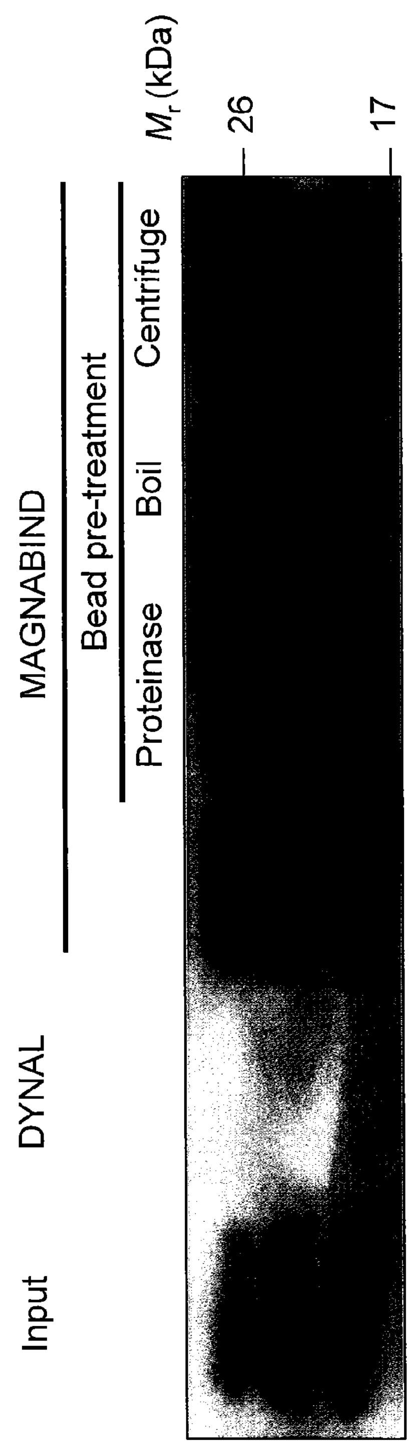
FIG. 2 shows binding of $PrP^{Sc}$ to MAGNABIND Protein A beads treated for protein disruption. MAGNABIND Protein A beads were pre-treated by Proteinase K digestion (25 μg/mL), boiled (95° C. for 10 minutes), or centrifuged (14,000×g for 10 minutes at 22° C.). Untreated control DYNAL Protein A and MAGNABIND Protein A beads were also tested. Following these treatments, beads were washed, and incubated with RML scrapie-infected mouse brain homogenate overnight. Bound $PrP^{Sc}$ molecules were detected by Proteinase K digestion and anti-PrP (6D11) immunoblot.
Figure 3A:
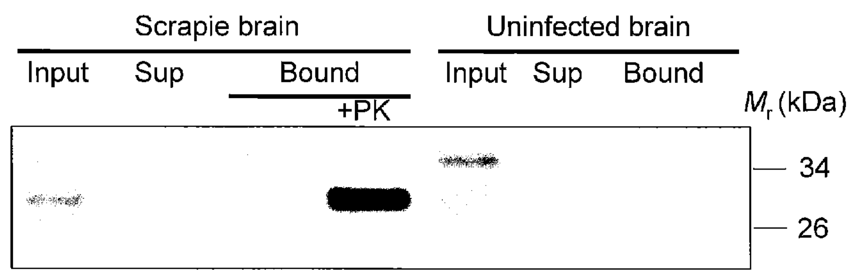
(FIG. 3A) Input, supernatant (Sup) and bound fractions were analyzed for PrP molecules by anti-PrP (6D11) immunoblot. The scrapie brain bound fraction was also analyzed for PrP by Proteinase K digestion (+PK).
Figure 3B:
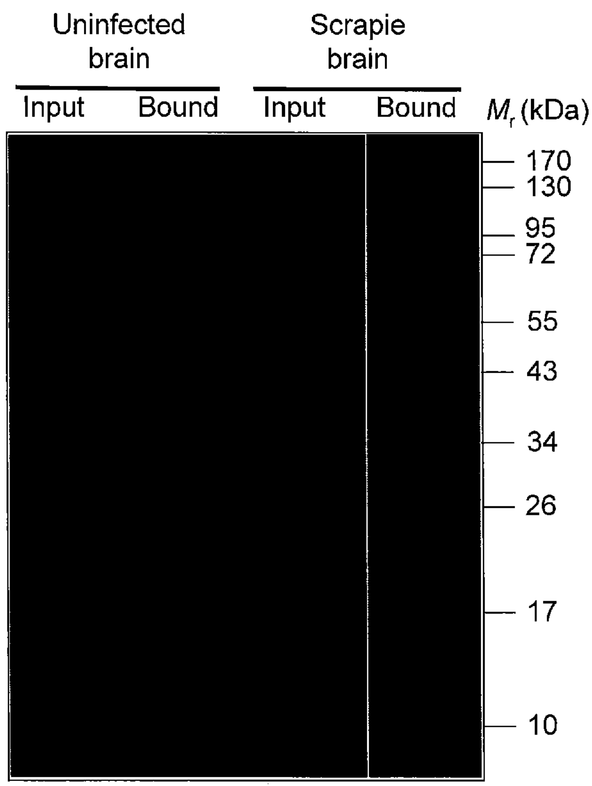
(FIG. 3B) Input and bound fractions were analyzed for total protein by silver staining. All samples were analyzed on the same gel, with white lines indicating excised intervening lanes.
Figures 4A, 4B:
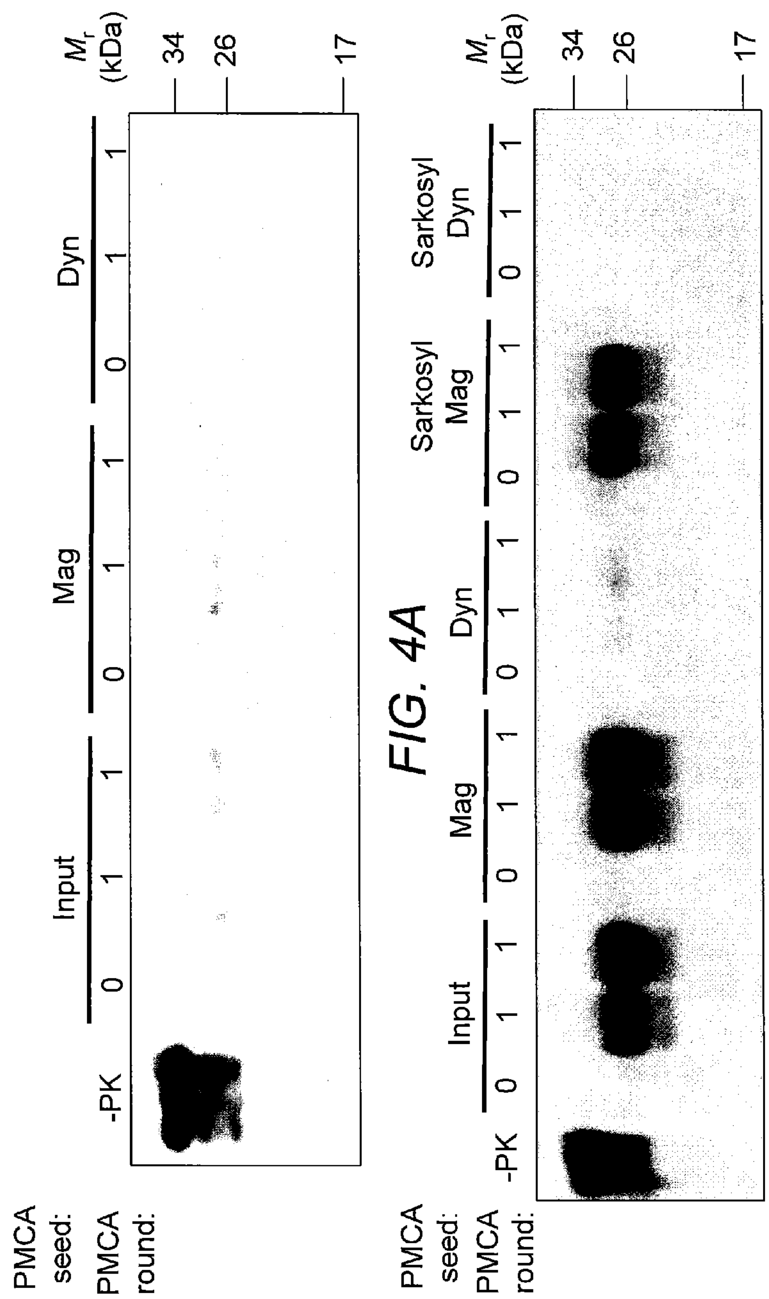
FIG. 4 shows protein misfolding cyclic amplification (PMCA) reactions seeded with MAGNABIND-bound $PrP^{Sc}$. RML mouse (FIG. 4A) or Sc237 hamster (FIG. 4B) brain homogenates before (input) or after binding by MAGNABIND Protein A beads (Mag) or by DYNAL Protein A (Dyn) were used to seed PMCA reactions. Normal mouse (FIG. 4A) or hamster (FIG. 4B) brain homogenates were used as substrate. Prior to PMCA, one set of beads was washed with Sarkosyl detergent (Sarkosyl, FIG. 4B). Each reaction mixture was analyzed before (–) or after (+) PMCA. $PrP^{Sc}$ molecules were detected by Proteinase K digestion and anti-PrP (6D11) immunoblot.
Figure 5:
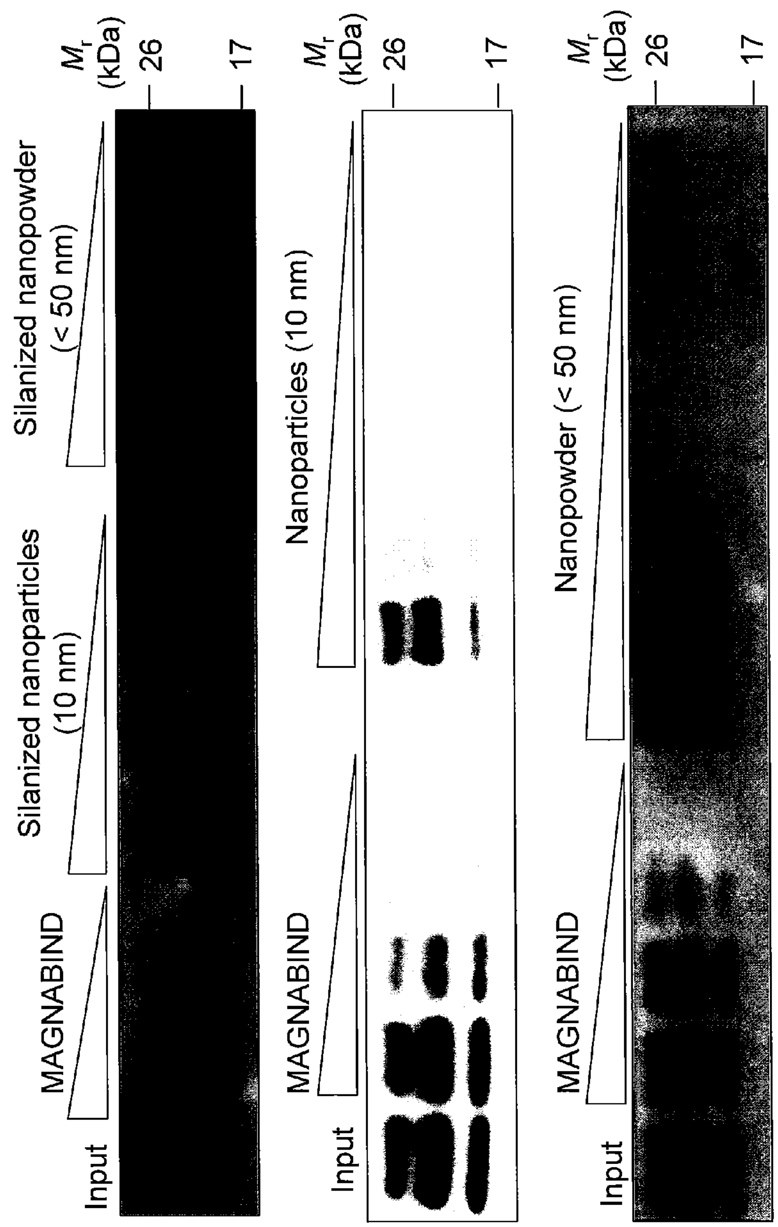
FIG. 5 binding of $PrP^{Sc}$ to MAGNABIND, silanized nano-magnetite, and unsilanized nano-magnetite. RML scrapie-infected mouse brain homogenate was incubated with various quantities of MAGNABIND Protein A beads (0.005-0.125 mg), silanized magnetite nanoparticles (10 nm size, 0.005-2 mg), silanized magnetite nanopowder (<50 nm size, 0.005-2 mg), unsilanized magnetic nanoparticles (0.0015-2 mg), or unsilanized magnetic nanopowder (0.0015-2 mg). $PrP^{Sc}$ molecules were detected by Proteinase K digestion and anti-PrP (6D11) immunoblot.
Figure 6:
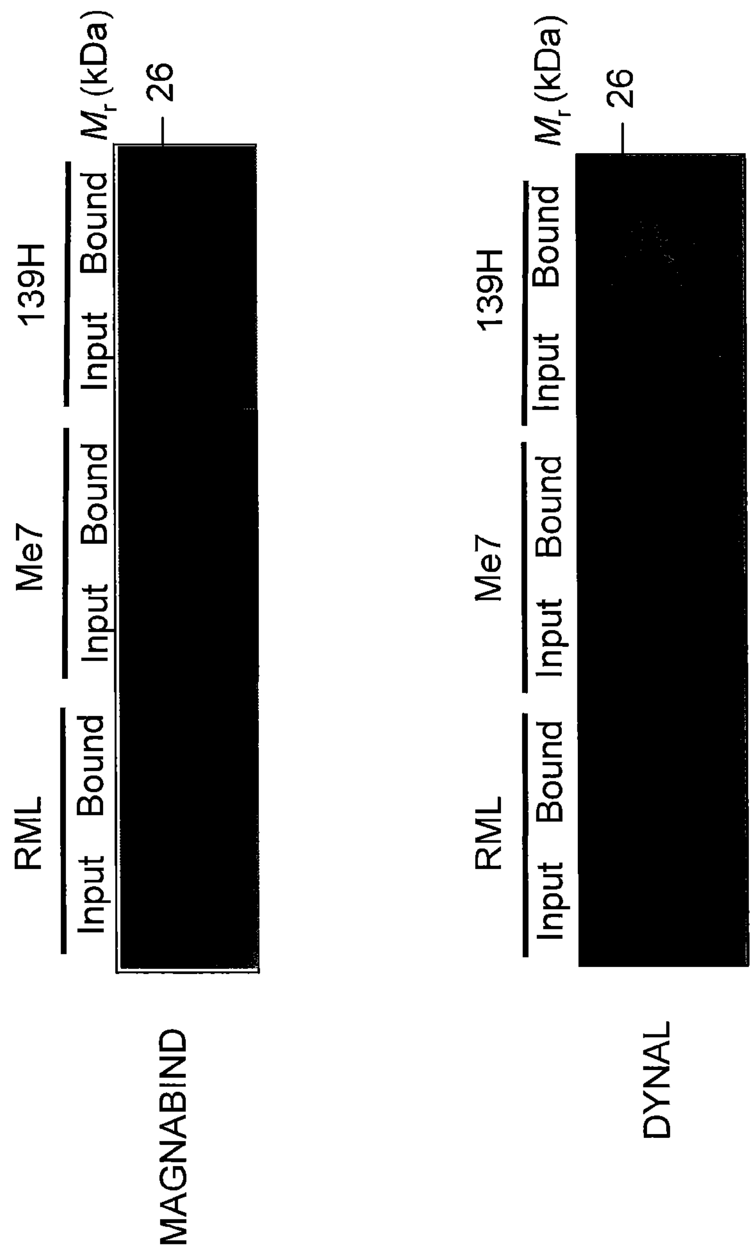
FIG. 6 shows binding of diverse strain $PrP^{Sc}$ molecules to MAGNABIND or DYNAL beads. Prion-infected brain homogenates from various strains (mouse RML, mouse Me7, hamster 139H) were incubated overnight with MAGNABIND Protein A or DYNAL Protein A beads. Input and bound $PrP^{Sc}$ molecules were detected by Proteinase K digestion and anti-PrP (6D11) immunoblot.

It has now been found that magnetic substrates, e.g., magnetic iron oxide substrates, non-covalently bind the infectious conformer of the prion protein, $Prp^{Sc}$, selectively and with high affinity (see FIGS. 1 and 2). Furthermore, immobilized $Prp^{Sc}$ serves as a competent seed for prion amplification techniques such as Protein Misfolding Cyclic Amplification (PMCA)(See FIG. 4). Moreover, magnetic substrates bind to $Prp^{Sc}$ molecules from a variety of prion isolates in different animal species (FIGS. 3 and 6), but do not bind the normal conformer of the prion protein, $Prp^{C}$, or the vast majority of other proteins. Immobilization of $Prp^{Sc}$ appeared to be independent of substrate size and coating (i.e., silanization) as silanized and unsilanized magnetic beads, nanoparticles or nanopowders could immobilize prion protein (see FIG. 5).

Accordingly, the present invention features methods for immobilizing infectious prion protein using a magnetic substrate, compositions containing substrate-bound $Prp^{Sc}$, and methods of using the same. The magnetic substrate of the invention can be ferromagnetic, paramagnetic or superparamagnetic. Paramagnetic materials are characterized by a weak, positive magnetic susceptibility and by their inability to remain magnetic in the absence of an applied magnetic field. Ferromagnetic materials have high, positive magnetic susceptibilities and maintain their magnetism in the absence of an applied field. Like paramagnetic materials, superparamagnetic materials are characterized by an inability to remain magnetic in the absence of an applied magnetic field. Superparamagnetic materials can have magnetic susceptibilities nearly as high as ferromagnetic materials and far higher than paramagnetic materials (Bean & Livingston (1959) *J. Appl. Phys*. 30(Suppl.):1205). In particular embodiments, the magnetic substrate of the invention is paramagnetic or superparamagnetic.

Paramagnetic substrates of the invention preferably contain transition metal ions, such as iron, manganese, gadolinium, and/or copper ions. Additional materials suitable for preparation of paramagnetic substrates include transition metals such as titanium, vanadium, chromium, cobalt, and nickel, lanthanide metals such as europium, and/or actinide metals such as protactinium. These metals may be independently selected or excluded for use in different embodiments of the invention. Paramagnetic ions have unpaired electrons, resulting in a positive magnetic susceptibility. Preferably, the paramagnetic substrates contain a relatively non-toxic metal such as iron.

Superparamagnetic substrates are composed of substances like ferrite which are ferromagnetic in bulk but which, because of the very small particle size, have lost their permanent magnetism. Generally, superparamagnetic particles have a particle size that ranges from about 30 to 50 nanometers (about 300 to 500 angstroms (Å)). Particles in this size range are impacted by both thermal effects, which quench the magnetic field, and magnetic ordering effects, with the result that the magnetic vector is unstable and fluctuates in the same way as for paramagnetic materials. Superparamagnetic materials possess high magnetic susceptibility and crystalline structures found in ferromagnetic materials, but rapidly lose their magnetic properties in the absence of an applied magnetic field. Superparamagnetic materials are preferably iron oxides such as iron hydroxide, iron oxides, iron oxide hydrates, or iron mixed oxides. Superparamagnetic particles exhibit stronger magnetic effects than paramagnetic particles of an equivalent size. For example, an iron oxide superparamagnetic particle may exhibit a magnetic field that is about 50,000 times stronger than the magnetic field exhibited by a similarly-sized gadolinium-based paramagnetic particle. Accordingly, in particular embodiments, the magnetic substrate of the invention contains an iron oxide.

Preferably, the magnetic substrate of the invention is a microparticle (e.g., a bead having a diameter in the range of 1 to 500 μm), nanoparticle ((e.g., a particle having a diameter in the range of 1 to 999 nm), or nanopowder. The selection of the magnetic substrate may be dependent on a number of factors including, e.g., the intended used of the substrate. For example, a microparticle may be desirable when the substrate is used for diagnostic detection of a prion disease or disinfection of a blood sample, whereas a nanoparticle or nanopowder may be desirable when the magnetic substrate is used in the treatment of prion diseases, i.e., such substrates would reduce the chance of triggering an immune response or thrombosis. Moreover, a small size helps to enhance the half life of the particles in circulation. The size of the magnetic nanoparticles may be controlled, for example, by selection of reaction conditions such as temperature, presence and type of stabilizing agent, ratio of metallic salts to surfactants, and the like. See, e.g., Murray, et al. (2001) *IBM. J. Res. Dev.* 45:47-56.

Substrates of the invention can be manufactured to be chemically and magnetically stable, and to have a high magnetic moment. Stability may optionally be enhanced, for example, by coating the magnetic substrate with a noble metal surface. Such a surface can improve both oxidative and magnetic stability. Methods of coating magnetic nanoparticles with a noble metal shell are known in the art. See, e.g., Park, et al. (2001) *J. Am. Chem. Soc.* 123:5743-5746.

As demonstrated herein, silanized magnetic substrates also selectively and efficiently bind infectious prion protein. Accordingly, the present invention also embraces the use of a magnetic substrate that is silanized. Silanization can be carried out as described herein or by any suitable conventional method using organic or inorganic molecules or with organic-inorganic mixed structures (Durdureanu-Angheluta, et al. (2008) *Dig. J. Nanomater. Biostruct.* 3:33-40). For example, magnetic substrates coated with 3-(trimethoxy-silyl)propyl methacrylate, 3-aminopropyltriethoxysilane, allyltriethoxysilane or methyltriethoxysilane can be used to confer a hydrophobic or hydrophilic nature to the magnetic substrates described herein and determine stability of the same in adequate solvents. Moreover, when the magnetic substrate of the invention is a nanoparticle or nanopowder, silanization promotes self-assembly of the nanoparticles or nanopowder thereby increasing their dimensions (Durdureanu-Angheluta, et al. (2008) supra).

The results herein demonstrate that contact of an infectious prion protein with a magnetic substrate (optionally silanized) non-covalently immobilizes the infectious prion protein. In this respect, the immobilization of an infectious prion protein in accordance with the present invention is carried out in the absence of a cross-linking agent or other functional or reactive group that covalently binds or has the potential to covalently bind (i.e., in the presence of a crosslinking agent) the prion protein to the magnetic substrate. Functional or reactive groups conventionally used in the art for covalent binding include, e.g., carbodiimides, ketones, imides, oximes, thioesters, thioamines, and the like. Examples of cross-linking agents include but are not limited to N-hydroxysuccinimide used in carbodiimide activation, dimethyl suberimidate, glyoxal, glutaraldehyde, epichlorohydrin, recombinant protein linkers or spacers and the like.

The analysis of biological samples (e.g., for research, diagnostic or forensic purposes) begins with complex mixtures such a blood, serum or cell suspensions that contain not only the analytes of interest, but also a great variety of constituents which may interfere with the intended analysis. As with standard analytical chemical separation, it is generally desirable if not necessary to separate the analyte fraction of sample from the remainder. The suitability of certain magnetic particles for this purpose has been widely documented in the prior art, said particles, when used in the microwell format, generally requiring a high magnetic susceptibility to permit their collection and immobilization within reasonable time in magnetic field gradients which may be generated in a laboratory setting by use of permanent magnets. In this regard, the immobilization of prion proteins with magnetic substrates is of particular use in methods of analyzing prion proteins, wherein prion proteins in a sample are immobilized with a magnetic substrate, the magnetic substrate is washed to remove mobile (non-immobilized) constituents of the original mixture and the bound prion protein is analyzed, e.g., by PMCA or immunoassay. In certain embodiments, magnetic capture of the magnetic substrate during wash cycles employs permanent magnets known in the prior art which achieve temporary immobilization. Moreover, miniaturization of the assay environment ensures that particles always reside within a short distance of typically not more than 100 μm from the nearest bounding surface of the reaction vessel, thereby reducing the time required to collect particles of given magnetic susceptibility from suspension into a magnetic gradient, or, conversely, to minimize the requisite magnetic susceptibility to ensure trapping within a given collection time, typically not more than 5 minutes and preferably not more than 0.5 minutes, by a magnetic field and field gradient of given strength.

In addition to diagnostic applications, immmobilization of prion proteins with magnetic substrates can be used to effectively remove infectious prion proteins from blood and/or plasma supplies. Moreover, it is contemplated that magnetic nanoparticles could be of use in capturing infectious prion protein in vivo thereby facilitating the prevention or treatment of a prion-associated disease. In each application, a sample (e.g., a blood sample) or subject (a subject diagnosed with an infectious prion protein) is provided with a magnetic nanoparticles so that the infectious prion protein binds to the magnetic nanoparticle and the infectious prion protein-bound magnetic nanoparticle is removed using, e.g., a magnet.

Example 1

Materials and Methods

Preparation of Scrapie-Infected and Uninfected Brain Homogenate. CD-1 Mouse (strains RML, Me7, and 301C) and Syrian hamster (Sc237, 139H, Drowsy) scrapie-infected brains were homogenized (Covidien tissue grinder, Mansfield, Mass.) to 10% in phosphate-buffered saline (PBS, pH 7.4; Cellgro, Manassas, Va.). Uninfected CD-1 mouse and Syrian hamster brains (Biochemed, Winchester, Va.) were homogenized in the same manner. Homogenates were initially clarified by centrifugation at 200×g for 30 seconds and stored at −70° C. Freshly clarified 5% homogenate for each experiment was prepared by adding an equal volume of tris-buffered saline (TBS: 50 mM Tris, 200 mM NaCl, pH 7.5), vortexing for 15 seconds, sonicating (Misonix 4000 with Microplate Horn; Qsonica, Newtown, Conn.) for 1 minute, and centrifuging at 500×g for 15 minutes.

Preparation of Nanoparticles and Nanopowder. Iron (II,III) oxide ($Fe_3O_4$, magnetite) 10 nm nanoparticles (Sigma, St. Louis, Mo.) in toluene were mixed with an equal volume of methanol, and separated by a Magnetic Particle Separator (PureBiotech, Middlesex, N.J.). Iron (II,III) oxide ($Fe_3O_4$, magnetite) <50 nm nanopowder was also obtained from Sigma. To silanize (Noren & Kempe (2009) *Int. J. Pept. Res. Ther.* 15:287-292), nanoparticles or nanopowder was resuspended in methanol to 0.11 mg/mL, to which was added 1/10 volume 3-(Trimethoxy-silyl)propyl methacrylate (Sigma). Each was sonicated for 1 minute at 70% power, then incubated for 4.5 hours at 25° C. with 300 rpm shaking. Each was then rinsed in methanol, then ethanol.

Binding Assays.

MAGNABIND (Pierce, Rockford, Ill.) or DYNAL (Invitrogen, Carlsbad, Calif.) magnetic beads, bearing either Protein A or Streptavidin, were magnetically separated from solution. Unless otherwise noted, 25 beads (5 μg/mL) were rinsed twice in 500 μL PBS, then incubated in 150 μL assay buffer (TBS, 1% TRITON X-100, 1% TWEEN 20) with 5 μL clarified 5% brain homogenate overnight at room temperature with 10 rpm end-over-end rotation. IgG 89-112 anti-$PrP^{Sc}$ antibody (Moroncini, et al. (2004) *Proc. Natl. Acad. Sci.* 101:10404-9) was added to designated samples at 7.5 μg/mL. Beads were separated from solution and rinsed twice in 500 μL wash buffer (TBS, 0.05% TWEEN 20) before analysis of bound molecules. $PrP^{Sc}$-$PrP^{C}$ comparison reactions were carried out in TBS with 3% NP-40 and 3% TWEEN 20 for 2 hours, followed by four 1 mL washes in TBS with 2% Sarkosyl.

Protein Misfolding Cyclic Amplification (PMCA). Following binding, samples were resuspended in 10% CD-1 mouse or Syrian hamster brain homogenate, which was prepared in Soto conversion buffer (PBS, 1% TRITON X-100, Roche Complete mini protease inhibitor; Castilla, et al. (2006) *Methods Enzymol.* 412:3-21) with additional 4 mM EDTA. One round of PMCA included 30 second microplate horn sonication pulses every 30 minutes for 24 hours at 90% power.

Prion Protein Detection.

Bound $PrP^{Sc}$ was detected by subjecting beads to limited proteolysis in 50 μL (25 μg/mL for mouse, 50 μg/mL for hamster) Proteinase K (Roche, Indianapolis, Ind.) in PBS, 1% TRITON X-100. Proteolysis proceeded for 30 minutes (mouse) or 60 minutes (hamster) at 37° C. and 750 rpm shaking, and was terminated by addition of 17 μL 4× sample buffer (217 mM tris pH 6.8, 8.7% (w/v) sodium dodecyl sulfate, 21% (v/v) glycerol, 0.02% (w/v) bromophenol blue, 3M β-mercaptoethanol) and 10-minute incubation at 95° C. PrP was detected by sodium dodecyl sulfate-polyacrylamide gel electrophoresis (SDS-PAGE), semi-dry transfer to PVDF membrane, immunoblot with anti-PrP antibody 6D11, horseradish peroxidase (HRP)-conjugated anti-mouse sheep antibody, and enhanced chemiluminescence (SUPERSIGNAL West Femto Substrate; Pierce, Rockford, Ill.). Signals were visualized by a FUJI (Fujifilm) LAS-3000 chemiluminescence documentation system.

Silver Stain Detection of Total Protein.

Following SDS-PAGE, the gel was fixed overnight in 50% ethanol/10% acetic acid, then treated with two 10 minute washes in 10% ethanol to remove SDS. Next, the gel was incubated for 2 minutes in Farmer's solution (0.3 g sodium thiosulfate, 0.15 g potassium ferricyanide, 0.05 g sodium carbonate in 100 mL water), followed by four 20-minute washes in water, then 12 minutes of silver staining (0.2 g silver nitrate in 100 mL water). Gel was then treated with developer (3 g sodium carbonate, 50 μL fresh 37% formaldehyde, 100 mL water) for a short rinse and subsequent approximate 8 min. incubation). Progression of staining was halted by addition of stop solution (5% acetic acid in water).

What is claimed is:

1. A method for immobilizing an infectious prion protein comprising contacting an infectious prion protein with a magnetic substrate that selectively immobilizes the infectious prion protein and not $PrP^c$ so that the infectious prion protein is immobilized.

2. The method of claim 1, wherein the magnetic substrate comprises an iron oxide.

3. The method of claim 1, wherein the magnetic substrate is silanized.

4. The method of claim 1, wherein the magnetic substrate is a microparticle, nanoparticle, or nanopowder.

5. The method of claim 1, wherein the infectious prion protein is present in a biological sample.

6. A complex comprising an infectious prion protein and a manufactured magnetic substrate, wherein the infectious prion protein is non-covalently bound to the substrate, in the absence of a cross-linking agent, so that the infectious prion protein is immobilized.

* * * * *

UNITED STATES PATENT AND TRADEMARK OFFICE

CERTIFICATE OF CORRECTION

PATENT NO. : 8,889,836 B2
APPLICATION NO. : 13/702673
DATED : November 18, 2014
INVENTOR(S) : Surachai Supattapone It is certified that error appears in the above-identified patent and that said Letters Patent is hereby corrected as shown below:

In the Claims:

Column 8, line 6, Claim 1, delete, "immobilized."

Column 8, line 6, Claim 1, add, --immobilized, wherein contact of the infectious prion protein with the magnetic substrate is carried out in the absence of a cross-linking agent.--

Signed and Sealed this
Twenty-fourth Day of February, 2015

Michelle K. Lee
*Deputy Director of the United States Patent and Trademark Office*